(12) United States Patent
Vicari et al.

(10) Patent No.: US 10,059,640 B2
(45) Date of Patent: Aug. 28, 2018

(54) APPARATUS AND PROCESS FOR THE PREPARATION OF ACETYLENE AND SYNTHESIS GAS

(71) Applicant: BASF SE, Ludwigshafen (DE)

(72) Inventors: Maximilian Vicari, Limburgerhof (DE); Susanne Britzius, Mannheim (DE); Lilian Kara-Hippen, Frankenthal (DE); Michael Russ, Roemerberg (DE); Matthias Kern, Deidesheim (DE); Christian Weichert, Deidesheim (DE)

(73) Assignee: BASF SE, Ludwigshafen (DE)

( * ) Notice: Subject to any disclaimer, the term of this patent is extended or adjusted under 35 U.S.C. 154(b) by 157 days.

(21) Appl. No.: 15/129,094

(22) PCT Filed: Mar. 25, 2015

(86) PCT No.: PCT/EP2015/056377
§ 371 (c)(1),
(2) Date: Sep. 26, 2016

(87) PCT Pub. No.: WO2015/144754
PCT Pub. Date: Oct. 1, 2015

(65) Prior Publication Data
US 2018/0170829 A1 Jun. 21, 2018

(30) Foreign Application Priority Data
Mar. 26, 2014 (EP) .................................... 14161692

(51) Int. Cl.
*C07C 11/24* (2006.01)
*C07C 2/78* (2006.01)
(Continued)

(52) U.S. Cl.
CPC .................. *C07C 2/78* (2013.01); *B01D 3/14* (2013.01); *C01B 3/36* (2013.01); *C07C 11/24* (2013.01);
(Continued)

(58) Field of Classification Search
CPC ... C07C 11/24; C07C 2/78; C01B 2203/0255; C01B 3/36; C01B 2203/04;
(Continued)

(56) References Cited

U.S. PATENT DOCUMENTS

| 3,396,207 A | 8/1968 | Bartholome et al. |
| 5,789,644 A | 8/1998 | Paessler et al. |
| 2015/0217999 A1 | 8/2015 | Vicari et al. |

FOREIGN PATENT DOCUMENTS

| DE | 875 198 | 4/1953 |
| DE | 1 051 845 | 3/1959 |

(Continued)

OTHER PUBLICATIONS

International Search Report dated Aug. 31, 2015 in PCT/EP2015/056377, filed Mar. 25, 2015.
(Continued)

*Primary Examiner* — Jafar Parsa
(74) *Attorney, Agent, or Firm* — Oblon, McClelland, Maier & Neustadt, L.L.P.

(57) ABSTRACT

An apparatus (10) for the preparation of acetylene and synthesis gas by partial oxidation of hydrocarbons with oxygen is proposed. The apparatus (10) comprises a reactor (12), wherein the reactor (12) comprises a burner block (14) with a furnace chamber for the preparation of a composition C1 comprising at least acetylene and substituted acetylene, a first scrubber (22) which is constructed for adding a solvent to the composition C1 to obtain a composition C2,
(Continued)

a second scrubber (26) which is constructed for adding the solvent to the composition C2 to obtain a composition C3, a first stripper (36) which is constructed for stripping the composition C3 to obtain a composition C4 comprising the substituted acetylene, acetylene and the solvent and for separating off the acetylene, a first column (46) which is constructed for partial degassing of the composition C4 under a pressure of from 1.0 bar to 1.5 bar to obtain a composition C5 and a first amount A1 of the solvent, a second stripper (56) to which the composition C5 can be fed for stripping a composition C9 to obtain a second amount A2 of the solvent and a composition C6, a third stripper (68) which is constructed for stripping the solvent from the first scrubber (22) to obtain a composition C9, wherein the third striper (68) is connected to the second stripper (56) for feeding the composition C9 to the second stripper (56), an apparatus (72) for adding a diluting gas to the composition C5, which is arranged between the first column (46) and the second stripper (56), a second column (76) which is constructed for adding water to the composition C6 to obtain a composition C7 comprising a third amount A3 of the solvent and water and to obtain a composition C8 comprising the substituted acetylene, and a mixing condenser (82) which is constructed for adding water to the composition C8 to obtain a composition C11 comprising the substituted acetylene.

A process for the preparation of acetylene and synthesis gas by partial oxidation of hydrocarbons with oxygen is further proposed.

17 Claims, 1 Drawing Sheet

(51) Int. Cl.
*B01D 3/14* (2006.01)
*C01B 3/36* (2006.01)
*C07D 207/267* (2006.01)
*C07C 15/073* (2006.01)
*C07C 15/06* (2006.01)
*C07C 9/04* (2006.01)
*C07C 9/06* (2006.01)
*C07C 11/04* (2006.01)
*C07C 9/14* (2006.01)
*C07C 15/58* (2006.01)
*C07C 15/04* (2006.01)
*C07C 15/08* (2006.01)

(52) U.S. Cl.
CPC . *C07D 207/267* (2013.01); *B01J 2219/00006* (2013.01); *C07C 9/04* (2013.01); *C07C 9/06* (2013.01); *C07C 9/14* (2013.01); *C07C 11/04* (2013.01); *C07C 15/04* (2013.01); *C07C 15/06* (2013.01); *C07C 15/073* (2013.01); *C07C 15/08* (2013.01); *C07C 15/58* (2013.01)

(58) Field of Classification Search
CPC ...... C01B 2203/0465; C01B 2203/062; C01B 2203/1235; C01B 2203/0877; C01B 2203/0883; C01B 2203/0805; B01J 2219/006; B01J 4/002; B01J 19/2415; B01J 19/248; B01J 2219/00054; B01J 2219/000157; B01J 2219/00279; B01J 2219/00905

See application file for complete search history.

(56) References Cited

FOREIGN PATENT DOCUMENTS

| | | |
|---|---|---|
| DE | 1 057 094 | 5/1959 |
| DE | 44 22 815 A1 | 1/1996 |
| WO | WO 2013/0186291 A1 | 12/2013 |
| WO | WO 2014/037311 A1 | 3/2014 |

OTHER PUBLICATIONS

International Preliminary Report on Patentability dated Sep. 29, 2016 in PCT/EP2015/056377 (with English language translation).

APPARATUS AND PROCESS FOR THE PREPARATION OF ACETYLENE AND SYNTHESIS GAS

The present invention relates to an improved apparatus and an improved process for the preparation of acetylene and synthesis gas by partial oxidation of hydrocarbons in a reactor, in which a stream containing the hydrocarbon and a stream containing the oxygen are passed into the reactor.

High temperature reactions for the partial oxidation of hydrocarbons are conventionally carried out in a reactor system of a mixing unit, burner block, furnace chamber and quenching installation. An example which may be mentioned of such a partial oxidation in the high temperature range is the preparation of acetylene and synthesis gas by partial oxidation of hydrocarbons. This is described, for example, in DE 875198, DE 1051845, DE 1057094 and DE 4422815.

The mixer/burner block/furnace chamber/quencher combinations—called reactor for simplification in the following when this combination is referred to—conventionally employed for the BASF-Sachsse-Bartholomé acetylene process is explained in these publications.

The starting substances, such as, for example, natural gas and oxygen, are heated up separately in this process, conventionally up to 600° C. The reactants are mixed intensively in a mixing zone, and after flowing through a burner block are subjected to an exothermic reaction in a furnace chamber. In these cases the burner block comprises a particular number of parallel channels in which the flow rate of the ignitable oxygen/natural gas mixture is higher than the flame propagation rate (rate of reaction, rate of conversion), in order to prevent the flame from breaking through into the mixing chamber. The metallic burner block is cooled in order to withstand the thermal stresses. Depending on the dwell time in the mixing chamber, there is the risk of pre-ignition and re-ignition due to the limited heat stability of the mixtures. The term ignition delay time or induction time is used here as that period of time in which an ignitable mixture undergoes no noticeable intrinsic thermal change. The induction time depends on the nature of the hydrocarbons employed, the state of the mixture and on the pressure and temperature. It determines the maximum dwell time of the reactants in the mixing chamber. Reactants such as hydrogen, liquefied gas or light gasoline, the use of which is particularly desirable because of increases in yield and/or capacity in the synthesis process, are distinguished by a comparatively high reactivity and therefore a short induction time.

The acetylene burners employed on the current production scale are distinguished by their cylindrical geometry of the furnace chamber. The burner block preferably has hexagonally arranged lead-through bores. In one embodiment e.g. 127 bores each with an internal diameter of 27 mm are arranged hexagonally on a circular base cross-section having a diameter of approx. 500 mm. As a rule the bore or channel diameters employed are about 19 mm to 27 mm. The subsequent furnace chamber in which the flame of the acetylene-forming partial oxidation reaction is stabilized is likewise of cylindrical cross-section, it is water-cooled and corresponds in appearance to that of a short tube (of e.g. 180 mm to 533 mm diameter and 380 to 450 mm length). So-called auxiliary oxygen is fed to the reaction space at the level of the surface of the burner block on the furnace chamber side.

This ensures stabilizing of the flame and therefore a defined distance from the flame root and therefore from the start of the reaction to the discontinuation of the reaction by the quenching installation. The entire burner of burner block and furnace chamber is suspended from the top in a quenching container of relatively large cross-section via a flange. At the level of the exit plane from the furnace chamber outside the circumference thereof there are installed quenching nozzles on one or more quenching distributor rings, which spray the quenching medium, e.g. water or oil, with or without the aid of a spraying medium, and inject it approximately perpendicularly to the main direction of flow of the reaction gases leaving the furnace chamber. This direct quencher has the task of cooling the reacting flow extremely rapidly to approx. 100° C. (water quenching) and 200° C. (oil quenching), so that secondary reactions, i.e. in particular the degradation of acetylene formed, are frozen. The range and distribution of the quenching jets here are ideally such that a temperature distribution which is as homogeneous as possible is achieved within the shortest possible time.

The acetylene burners employed on the current production scale are distinguished by a cylindrical geometry of the furnace chamber. The starting substances are premixed via a diffuser and fed to the burner block via hexagonally arranged lead-through bores, backmixing being avoided. In the known processes premixing of the starting substances takes place in the mixing diffuser in a relatively large volume and under high preheating temperatures.

In the technical process described, as well as acetylene substantially hydrogen, carbon monoxide and carbon black are formed in the reaction. As a result of the reaction, the process gas formed in this way furthermore comprises substituted acetylenes and BTX aromatics (BTX—benzene, toluene and xylenes). Of the BTX aromatics, benzene, toluene, xylene isomers, styrene and indene form the majority. Acetylene tends towards sudden spontaneous decomposition even at low temperatures. For safety reasons acetylene partial pressures of 1.4 bar should not be exceeded without further safety precautions. Separation by distillation methods is therefore ruled out. To separate off acetylene from gas mixtures, in particular those which have been obtained by thermal or electrical cracking of hydrocarbons with or without oxygen, it is known to isolate acetylene from acetylene-containing gases by scrubbing these gases with a solvent which has a high solubility for acetylene and then to gas the pure or highly enriched acetylene out of the acetylene-containing solution by several stages of applying reduced pressure or elevated temperature or by both measures. The solubility of acetylene in the solvents under S.T.P. is between 15 and 35 $m^3/m^3$ of absorbent. Because of the relatively low solubility of acetylene, this is economical only under high pressures, and for this reason the process gas must be compressed. The upper limit is determined by the maximum partial pressure of acetylene of 1.4 bar due to the risk of explosion.

The profitability of such a process is in doubt since it presents difficulties in freeing the solvent completely from the acetylene in the gassing out stage. If the pressure is lowered too much, e.g. below 0.1 bar, in order to achieve this aim, the expenditure for compression of the gassed-out acetylene is too high. Heating of the wash liquid to a high temperature, for example above 100° C., is expensive, and moreover associated with the risk of decomposition of the scrubbing liquid and the dissolved gas. It is further known that acetylene can be isolated from gas mixtures very easily and under economically favorable conditions if a scrubbing liquid is used which, in addition to water, contains more than 50% of an organic solvent which readily dissolves acetylene, is miscible with water and has a higher boiling point than water. The washed-out acetylene can be gassed out very easily and completely from such scrubbing liquids by evaporating some of the water out of the scrubbing liquid under an economically acceptable reduced pressure, such as, for example, approximately 0.2 to 0.5 bar, and freeing the scrubbing liquid from the acetylene by the ascending vapors in a counter-current column. Co-using water offers the advantage that the losses caused by saturation of the gas which has been freed from the acetylene and of the pure or enriched acetylene with the vapor of the solvent can be avoided by scrubbing these gases with a small amount of water, which removes this solvent. The aqueous solutions of the solvent which are thereby obtained can be added to the main amount of the organic solvent in order to keep the water content thereof at the desired level. Among the substances which are suitable as organic solvents, for example, butyrolactone, N-methyl-2-pyrrolidone, methanol, ammonia or dimethylformamide can be employed.

The kinetics of acetylene formation always lead to the formation of substituted acetylenes as by-products, chiefly diacetylene, methylacetylene and vinylacetylene. These components polymerize very rapidly and must be removed from the process gas as quickly as possible. Since they have a much better solubility in the absorbent than acetylene, it is sufficient to prescrub the process gas with a small amount of solvent before it enters into the acetylene isolation stage.

The absorbent N-methyl-2-pyrrolidone is employed in order to separate the process gas into three streams. Substituted acetylenes and aromatic compounds, which are the most soluble constituents of the cracked gas, the valuable product acetylene, which has a poorer solubility that the substituted acetylene but significantly better solution properties that the remaining constituents of the cracked gas, the so-called lean gas, which comprises chiefly hydrogen and carbon monoxide.

In the prescrubber the process gas is conventionally brought into contact with a small amount of solvent in order to separate off virtually all the aromatic compounds and C4 and substituted acetylenes, apart from vinylacetylene. In the main scrubber the gas is brought into contact with a significantly larger amount of N-methyl-2-pyrrolidone, which dissolves the acetylene, the remaining substituted acetylenes and some carbon monoxide. The lean gas leaves the column at the top. The N-methyl-2-pyrrolidone solution is degassed in several step in which the pressure is reduced and the temperature is increased. The stripper operates slightly above ambient pressure and temperature. In this column the loaded absorbent is brought into contact in counter-current with the gas from the subsequent degassing step. For this, the vapor stream from the vacuum column is brought to the operating pressure in the stripper by means of a vacuum machine before entry into the stripper. Carbon dioxide, which is the gas with the poorest solubility, is released at the top of the stripper in this manner. The carbon dioxide is recycled to the intake side of the compressor. The valuable product acetylene is taken off as a side stream of the stripper. The N-methyl-2-pyrrolidone solution is then degassed completely in two further stages at 110-120° C., first under atmospheric pressure and then under a lower pressure. Vinylacetylene, methylacetylene and excess process water are removed from the vacuum column as a side take-off. The water content of the solvent is monitored by the evaporator output in the vacuum column. The degassing is concluded in the bottom of the column and the solvent is cooled and recycled to the main scrubber.

The small amount of solvent from the prescrubber is stripped with crude synthesis gas in order to drive out dissolved acetylene and to recycle the vapor stream to the intake side of the compressor. The solvent is then degassed completely in the vacuum stripper, the gaseous removal stream from the vacuum column, which contains the excess process water and some substituted acetylenes, flowing in counter-current to the solvent. The vapor of the vacuum stripper contains the higher acetylenes, water and some N-methyl-2-pyrrolidone vapor. In a side column the N-methyl-2-pyrrolidone is back-scrubbed with a little water and the water/N-methyl-2-pyrrolidone mixture is fed to the main solvent stream. The gas is cooled by direct contact with water in the mixing condenser in order to condense out the majority of the water vapor. The substituted acetylenes are diluted before the vacuum pump with e.g. natural gas or lean gas. The diluted substituted acetylenes, which at this point are under slight increased pressure, can be used as combustion gas. In order to introduce as little water vapor as possible into the combustion, the substituted acetylenes are cooled again in a subsequent gas cooler downstream of the vacuum pump in order to condense out water vapor. For this, the gas is cooled directly in counter-current with circulating water. It is then diluted further with e.g. natural gas or lean gas and passed to the combustion. In order to minimize the polymer content of the solvent, about 2% of the amount of the solvent of the vacuum stripper circulation is taken off continuously and distilled off under reduced pressure.

In spite of the advantages arising from these processes and apparatuses, there is still potential for improvement. Thus, in the existing process for acetylene synthesis by partial oxidation according to Sachsse-Bartholomé with water quenching and oil quenching, the acetylenes and substituted acetylenes are separated off from the solvent N-methyl-2-pyrrolidone for the purpose of isolation of acetylene and solvent regeneration. The desorption of the process gas components dissolved in the prescrubber and main scrubber and the regeneration of the N-methyl-2-pyrrolidone circulations are carried out according to the state of the art in vacuo under approx. 150 to 500 mbar (abs.), usually under 200 mbar (abs.), in the vacuum column and in the gas path for the substituted acetylenes, which comprises inter alia a vacuum stripper, gas scrubber for N-methyl-2-pyrrolidone and a mixing condenser. This procedure leads to high investment costs in machines and apparatuses in this part of the installation, i.e. for the apparatuses for generating reduced pressure in the installation.

It is therefore the object of the present invention to provide an apparatus and a process for the preparation of acetylene and synthesis gas which at least largely avoids the disadvantages described above and which in particular allow a simpler mode of operation under normal pressure or slight increased pressure and thus a vacuum-free mode of operation.

An apparatus according to the invention for the preparation of acetylene and synthesis gas by partial oxidation of hydrocarbons with oxygen comprises a reactor, wherein the reactor comprises a burner block with a furnace chamber for preparation of a composition C1 comprising at least acetylene and substituted acetylene. The apparatus furthermore comprises a first scrubber which is constructed for adding a solvent to the composition C1 to obtain a composition C2. The apparatus furthermore comprises a second scrubber which is constructed for adding the solvent to the composition C2 to obtain a composition C3. The apparatus furthermore comprises a first stripper which is constructed for stripping the composition C3 to obtain a composition C4 comprising the substituted acetylene, acetylene and the solvent and for separating off the acetylene. The apparatus furthermore comprises a first column which is constructed for partial degassing of the composition C4 under a pressure of from 1.0 bar to 1.5 bar to obtain a composition C5, a composition C10 and a first amount A1 of the solvent. The apparatus furthermore comprises a second stripper to which the composition C5 can be fed for stripping a composition C9 to obtain a second amount A2 of the solvent and a composition C6. The apparatus furthermore comprises a third stripper which is constructed for stripping the solvent from the first scrubber to obtain a composition C9, the third stripper being connected to the second stripper for feeding the composition C9 to the second stripper. The apparatus furthermore comprises an apparatus for adding a diluting gas to the composition C5, which is arranged between the first column and the second stripper. The apparatus furthermore comprises a second column which is constructed for adding water to the composition C6 to obtain a composition C7 comprising a third amount A3 of the solvent and water and to obtain a composition C8 comprising the substituted acetylene. The apparatus furthermore comprises a mixing condenser which is constructed for adding water to the composition C8 to obtain a composition C11 comprising the substituted acetylene.

In the context of the present invention substituted acetylene is to be understood as meaning acetylene in which a hydrogen atom is substituted. In the context of the present invention this is, in particular, monosubstituted acetylene. The hydrogen atom is substituted in particular by an alkyl, alkenyl or alkynyl radical. The alkyl radical can be, in particular, methyl, the alkenyl radical can be, in particular, vinyl and the alkynyl radical can be, in particular, ethynyl. The substituted acetylene of the present invention is thus predominantly, but not exclusively, methylacetylene, vinylacetylene and diacetylene.

In the context of the present invention a solvent is to be understood as meaning in principle any solvent which has a solubility for acetylene and substituted acetylene. In particular, organic solvents which are miscible with water and have a higher boiling point than water can be employed in the context of the present invention.

In the context of the present invention stripping is to be understood as meaning a separation process, in particular a physical separation process, in which substances are transferred from a liquid phase into the gas phase by desorption operations. In this context the liquid phase is brought into contact with a gas, the so-called stripping gas, in the counter-current principle. Desorption in this context is to be understood as meaning an operation in which gas components bonded in the liquid are driven out of this liquid by a stripping gas by reducing the pressure and/or increasing the temperature and/or reducing the partial pressure. Desorption is thus the reverse operation to absorption.

Correspondingly, in the context of the present invention a stripper is to be understood as meaning an apparatus which is constructed and suitable for stripping. The stripper can be constructed, for example, in the form of a column. Via a nozzle or a liquid distributor, the liquid conveyed is finely divided at the top or top end of the stripper such that this trickles in the column into the bottom, in particular over packing, structured packing or trays. The stripping gas is conveyed through the stripper in counter-current. The packing serves to finely divide the liquid and thus to maximize the phase interface. Packing serves to increase the active surface area with a simultaneously low flow resistance. Packing is produced from various materials, depending on the intended use, such as, for example, rust-free steel, plastic or from ceramic. In the context of the present invention packing of rust-free steel is preferably employed.

In the context of the present invention a column is to be understood as meaning a process engineering apparatus in the form of a hollow, slender column with internal baffles which are required on the basis of the intended use or the operating conditions. In the context of the present invention the column serves to separate substance mixtures by diverse thermal processes. Physical properties and states of equilibrium between different phases are utilized for this. In the column, two phases are brought directly into contact with one another in counter-current. Baffles in the column serve to increase exchange of material and exchange of energy between the phases or avoid back-mixing.

In the context of the present invention a mixing condenser is to be understood as meaning an apparatus which is constructed and suitable for condensing of gases or vapors in direct contact with cooling water. The cooling water and condensate are thereby mixed.

The pressures mentioned in the context of the present invention are absolute pressure, unless explicitly described otherwise. The unit stated for the pressure is "bar" or "mbar", and for illustrating the absolute pressure can also be stated as "bar (abs.)" or "mbar (abs.)". As a rule, only the unit "bar" or "mbar" is stated here for abbreviation.

The diluting gas can be selected from the group consisting of: $H_2$, $N_2$, $CO_2$, $NH_3$, lean gas, natural gas. For example, when energy is introduced into the bottom of the first column is omitted and evaporation of water and N-methyl-2-pyrrolidone is therefore absent, the diluting gas is metered directly into the first column for holding the pressure in the first column. This ensures that the concentration of the gas of the substituted acetylenes in the side take-off is below the decomposition limit.

The second amount A2 of the solvent obtained from the second stripper can be fed to the first and/or second scrubber. The amount of solvent employed is thus reduced, since the solvent is mostly recovered by the apparatus according to the invention.

The first amount A1 of the solvent obtained from the first column can be fed to the first and/or second scrubber. The amount of solvent employed is thus reduced, since the solvent is mostly recovered by the apparatus according to the invention.

The first column can have a side take-off for leading off the composition C5. Preferably, the apparatus for adding a diluting gas to the composition C5 is adjacent to the side take-off. In this context the enriched vinylacetylene, the acetylene losses and N-methyl-2-pyrrolidone vapor and water vapor are taken off through the vaporous side take-off. This stream, which according to the state of the art is under about 200 mbar (abs.) and at about 100° C., changes only slightly in composition and in the apparatus according to the invention is under about 1.4 bar (abs.) and at approx. 150° C. In the case where this stream is dry, a critical deflagration pressure of <0.5 bar (abs.) is calculated, and is thus exceeded by the operating pressure in the column. The stream must therefore be diluted to a critical deflagration pressure of >1.5 bar (abs.). The concept according to the invention provides for a diluting gas being metered into the side take-off between the first column and the second stripper. By arranging the apparatus for adding a diluting gas to the composition C5 in the vicinity of the side take-off, the pressure can be controlled particularly readily and rapidly.

A temperature can be established in the mixing condenser for preventing a precipitation of naphthalene. For example, the temperature in the mixing condenser is to be established at between 40° C. and 80° C. Preferably, the temperature is 60° C. to 70° C., for example 65° C.

The second stripper can be operated under a pressure of from 1.0 bar to 1.4 bar for degassing the composition C9. The apparatus according to the invention thus allows a vacuum-free mode of operation. The economic potential lies in the reduction of the investment costs by the omission of vacuum units including the peripheral cooling installations by a process concept which can be realized safely.

The solvent can be N-methyl-2-pyrrolidone. Alternatively, other organic solvents can be used, such as, for example, butyrolactone, methanol, ammonia or dimethylformamide.

A process according to the invention for the preparation of acetylene and synthesis gas by partial oxidation of hydrocarbons with oxygen comprises the following steps, preferably in the stated sequence:
  partial oxidation of hydrocarbons with oxygen for the preparation of a composition C1 comprising at least acetylene and substituted acetylene,
  addition of a solvent to the composition C1 to obtain a composition C2,
  addition of the solvent to the composition C2 to obtain a composition C3,
  stripping of the composition C3 to obtain a composition C4 comprising the substituted acetylene, acetylene and the solvent and separating off the acetylene from the composition C3,
  partial degassing of the composition C4 under a pressure of from 1.0 bar to 1.5 bar to obtain a composition C5 and a first amount A1 of the solvent,
  stripping of a composition C9 with the composition C5 to obtain a second amount A2 of the solvent and a composition C6,
  stripping of the solvent obtained after preparation of the composition C1 to obtain the composition C9,
  addition of a diluting gas to the composition C5,
  addition of water to the composition C6 to obtain a composition C7 comprising a third amount A3 of the solvent and water and to obtain a composition C8 comprising the substituted acetylene, and
  addition of water to the composition C8 to obtain a composition C11 comprising the substituted acetylene.

The diluting gas can be selected from the group consisting of: $H_2$, $N_2$, $CO_2$, $NH_3$, lean gas, natural gas. For example, when energy is introduced into the bottom of the first column is omitted and evaporation of water and N-methyl-2-pyrrolidone is therefore absent, the diluting gas is metered directly into the first column for holding the pressure in the first column. This ensures that the concentration of the gas of the substituted acetylenes in the side take-off is below the decomposition limit.

The second amount A2 of the solvent obtained can be fed to the composition C1 and/or C2. The amount of solvent employed is thus reduced, since the solvent is mostly recovered by the apparatus according to the invention.

The first amount A1 of the solvent obtained can be fed to the composition C1 and/or C2. The amount of solvent employed is thus reduced, since the solvent is mostly recovered by the apparatus according to the invention.

A temperature of the composition C11 can be established for preventing a precipitation of naphthalene. For example, the temperature in the mixing condenser is to be established at between 40° C. and 80° C. Preferably, the temperature is 60° C. to 70° C., for example 65° C.

The composition C9 can be degassed under a pressure of from 1.0 bar to 1.4 bar. The process according to the invention thus allows a vacuum-free mode of operation. The economic potential lies in the reduction of the investment costs by the omission of vacuum units including the peripheral cooling installations by a process concept which can be realized safely.

The solvent can be N-methyl-2-pyrrolidone. Alternatively, other organic solvents can be used, such as, for example, butyrolactone, methanol, ammonia or dimethylformamide.

A basic concept of the present invention is a stripping of the loaded solvent, which is preferably N-methyl-2-pyrrolidone, under normal pressure or a slight increased pressure, such as, for example, approximately 1.1-1.4 bar (abs.), preferably 1.25 bar (abs.) and thus a vacuum-free mode of operation. The economic potential of the invention lies in the reduction of the investment costs by the omission of two vacuum units including the peripheral cooling installations by a process concept which can be realized safely. In the development of the novel process, nothing has changed in the connection of the individual apparatuses apart from the omission of the vacuum units together with the following cooling installations. The main flow path is retained almost completely, the operating conditions of pressure and temperature being adapted to the normal pressure procedure. Only the dilution of the gas containing the substituted acetylenes for lowering the partial pressure and therefore the stabilizing of the gas containing the substituted acetylenes no longer takes place after cooling in the mixing condenser and before the compression but between the gas take-off from the side of the first column and the second stripper, preferably directly after the side take-off. The target requirement is the release pressure of the gas containing the substituted acetylenes with 1.2 bar (abs.). The pressure in the upstream apparatuses are defined via the expected pressure loss chain.

The most important new challenge from the change in the process is the estimation of the risk of the novel concept in handling the material hazards of acetylene and the substituted acetylenes due to their tendency towards explosive spontaneous decomposition. An inventive feature of the process according to the invention is a process concept which can be realized safely without reservation. For evaluation of the safety of individual process streams, the planned process pressure was compared with the corresponding critical deflagration pressure. The Le Chatelier calculations—without water vapor partial pressure—are taken as the basis.

In the first column the N-methyl-2-pyrrolidone loaded with acetylene and vinylacetylene (main constituents) is regenerated, i.e. by introduction of energy into the bottom evaporator stripping vapor is generated, which frees the loaded N-methyl-2-pyrrolidone from the absorbed components via the top and side take-off and establishes it at a predetermined water content. In this context the enriched vinylacetylene, the acetylene losses and N-methyl-2-pyrrolidone vapor and water vapor are taken off by the vaporous side take-off. This stream, which according to the state of the art is under about 200 mbar (abs.) and at about 100° C., changes only slightly in composition and is then under about 1.4 bar (abs.) and at approx. 150° C. In the case where this stream is dry, a critical deflagration pressure of <0.5 bar (abs.) is calculated, and is thus exceeded by the operating pressure in the column. The stream must therefore be diluted to a critical deflagration pressure of >1.5 bar (abs.). The concept according to the invention provides for a diluting gas being metered into the side take-off between the first column and the second stripper. The desensitizing influence of diluting gases increases on the basis of their thermal capacity in the sequence $H_2<N_2<CO_2<NH_3$. The following gases inter alia can be employed as the diluting gas: $H_2$, $N_2$, $CO_2$, $NH_3$, lean gas, natural gas and others. The concept according to the invention provides for the diluting gas being metered directly into the column for holding the pressure in the column when introduction of energy into the bottom of the column is omitted and evaporation of water and N-methyl-2-pyrrolidone is therefore absent. This ensures that the concentration of the gas containing the substituted acetylenes in the side take-off is below the decomposition limit.

Corresponding to the first column, in the second stripper the loaded N-methylpyrrolidone from the first scrubber is regenerated, i.e. in addition to the intrinsic generation of vapor by introduction of energy into the bottom evaporator, the gaseous side take-off of the first column is fed into the bottom. The gas stream taken off via the top contains, in addition to N-methyl-2-pyrrolidone vapor and water vapor, the highest concentration of the gas containing the substituted acetylenes in the process. It is diluted by addition of a predetermined amount of diluting gas. The critical deflagration pressure of >1.5 bar (abs.) calculated for the (theoretically) dry stream is above the operating pressure of the column. For the second column following in the gas path of the gas containing the substituted acetylenes and for the mixing condenser, approximately the same differences between the calculated critical deflagration pressure of the gas streams and the process pressure result from the dilution. The procedure under normal pressure makes the gas machine for the gas containing the substituted acetylenes and the gas cooler for the gas containing the substituted acetylenes superfluous. The critical point for naphthalene is thereby shifted into the mixing condenser. If more naphthalene than is to be transported in the gas stream is present under a given pressure and temperature, i.e. if the partial pressure is higher than the sublimation pressure, naphthalene resublimes and precipitates out as a solid. By an appropriate temperature program, in particular temperatures of between 40° C. and 80° C. and preferably between 60° C. and 70° C., for example 65° C., the precipitation of naphthalene can be avoided. Downstream of the mixing condenser, the distance from the dew point is increased by dilution with e.g. natural gas or lean gas, so that condensation on the way to the torch can be avoided.

Further optional details and features of the present invention emerge from the following description of preferred examples, which are shown as a diagram in the drawing.

The drawing shows:

EMBODIMENTS OF THE INVENTION

Figure 1:
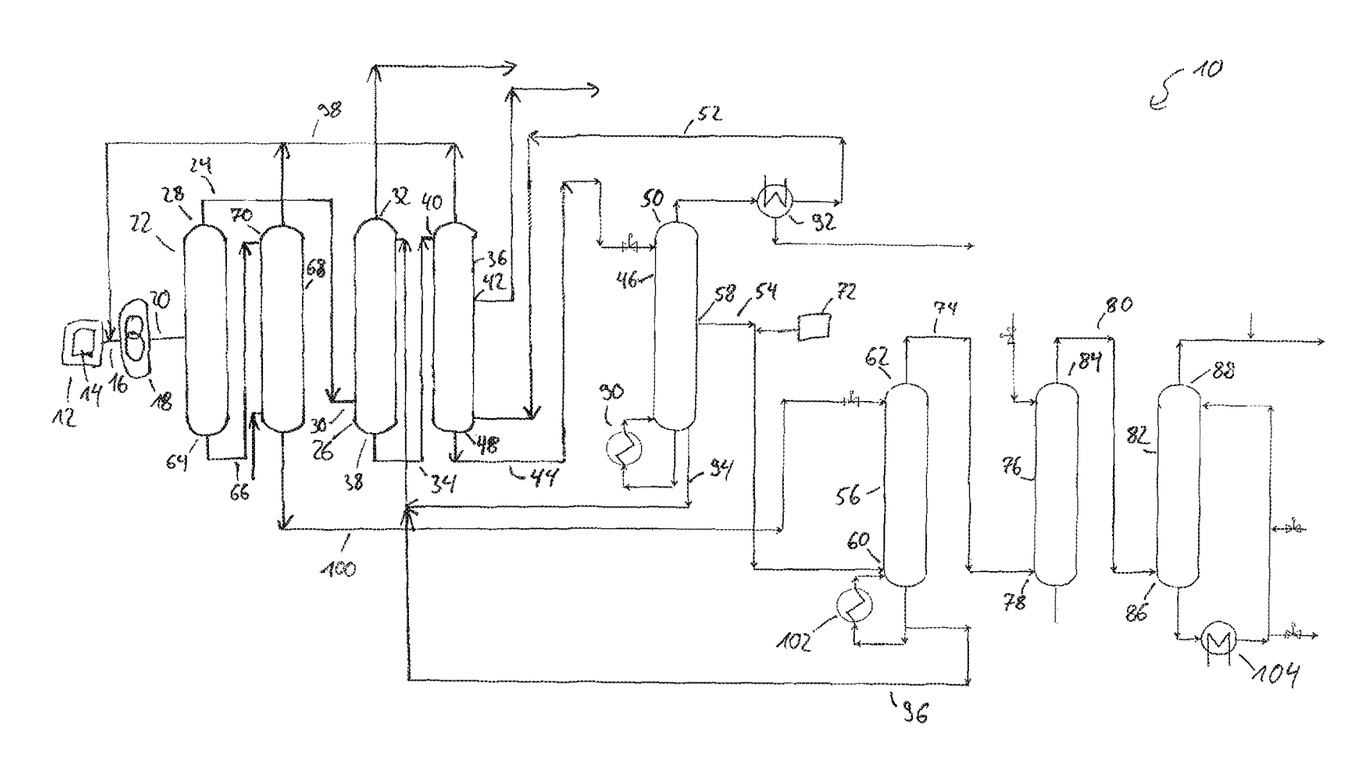
FIG. 1 a process engineering flow diagram of an apparatus according to the invention for the preparation of acetylene and synthesis gas by partial oxidation of hydrocarbons with oxygen.

FIG. 1 shows a flow diagram of an apparatus 10 according to the invention for the preparation of acetylene and synthesis gas by partial oxidation of hydrocarbon with oxygen. The apparatus 10 comprises a reactor 12. The reactor 12 comprises a burner block 14 with a furnace chamber, not shown in more detail, for the preparation of acetylene. For the preparation of acetylene and synthesis gas by partial oxidation, a stream containing hydrocarbon and a stream containing oxygen can be fed to the reactor 12.

The reactor 12 and in particular the burner block 14 are connected to a compressor 18 via a line 16. The compressor 18 is connected to a first scrubber 22 via a line 20. The first scrubber 22 can be constructed, for example, as a prescrubber. The first scrubber 22 is connected to a second scrubber 26 via a line 24. The second scrubber 26 can be constructed, for example, as the main scrubber. The line 24 extends from a top end 28 of the first scrubber 22 to a lower side end 30 of the second scrubber 26. The second scrubber 26 is constructed such that a so-called lean gas, which comprises chiefly hydrogen and carbon monoxide, can be removed or led away at a top end 32 of the second scrubber 26. The second scrubber 26 is connected to a first stripper 36 via a line 34.

In the example shown the first stripper 36 is constructed as a counter-current stripper. The line 34 extends from a lower end 38 of the second scrubber 26 to a top end 40 of the first stripper 36. The first stripper 36 is constructed such that acetylene can be separated off in the first stripper 36. The acetylene can be taken off, for example, as a side stream on one side 42 of the first stripper 36.

The first stripper 36 is connected to a first column 46 via a line 44. The line 44 extends from a lower end 48 of the first stripper 36 to a top end 50 of the first column 46. The line 44 leaves, for example, at a lowest point of the first stripper 36 and leads to a side intake at the top end 50 of the first column 46. The first column 46 is additionally connected to the first stripper 36 via a line 52. The line 52 extends from the top end 50 of the first column 46 to the lower end 48 of the first stripper 36. The line 52 leaves, for example, at a highest point of the first column 46 and leads to a side intake at the lower end 48 of the first stripper 36.

The first column 46 is connected to a second stripper 56 via a line 54. The line 54 extends from a side take-off 58 of the first column 46 to a lower end 60 of the second stripper 56.

The second stripper 56 further has a top end 62. A lower end 64 of the first scrubber 22 is connected to a third stripper 68 via a line 66. The line 66 extends from the lower end 64 of the first scrubber 22 to a top end 70 of the third stripper 68. For example, the line 66 leaves at a lowest point of the first scrubber 22.

An apparatus 72 is arranged between the first column 46 and the second stripper 56. The apparatus 72 is arranged more precisely in the vicinity of the side take-off 58 of the first column 46. The apparatus 72 is constructed for feeding a diluting gas to the line 54. The diluting gas is selected from the group consisting of $H_2$, $N_2$, $CO_2$, $NH_3$, lean gas and natural gas. The second stripper 56 is connected to a second column 76 via a line 74. The line 74 extends from the top end 62 of the second stripper 56 to a lower end 78 of the second column 76. For example, the line 74 leaves at a highest point of the second stripper 56 and leads to a side intake at the lower end 78 of the second column 76. The second column 76 is connected to a mixing condenser 82 via a line 80. The line extends from a top end 84 of the second column 76 to a lower end 86 of the mixing condenser 82. For example, the line 80 leaves from a highest point of the second column 76 and leads to a side intake at the lower end 86 of the mixing condenser 82. The mixing condenser 82 is constructed such that the substituted acetylene can be removed at a top end 88 of the mixing condenser 82.

A possible mode of operation according to the invention of the apparatus 10 is described in the following. A stream containing hydrocarbon and a stream containing oxygen are fed to the reactor 12. The two streams react with one another in the reactor 12. Acetylene is mostly formed in a reaction of the hydrocarbon with the oxygen in the reactor 12.

However, not exclusively acetylene is prepared by the partial oxidation of hydrocarbon and oxygen.

The kinetics of acetylene formation also always lead to the formation of substituted acetylenes as by-products. The substituted acetylenes include chiefly diacetylene, methylacetylene and vinylacetylene. More precisely, a the composition C1 which comprises at least acetylene and substituted acetylene is thus prepared. Since the substituted acetylenes polymerize very rapidly, they must be removed from the process gas or the composition C1 as quickly as possible. Unless stated otherwise, the expressions "substituted acetylene" and "substituted acetylenes" are used synonymously in the following in order to express that the composition C1 comprises at least one substituted acetylene.

The composition C1 is fed to the compressor 18 via the line 16 and compressed there. The composition C1 is then fed to the first scrubber 22 via the line 20. In the first scrubber 22, a solvent, such as, for example, N-methyl-2-pyrrolidone, is added to the composition C1. The solvent serves as an absorbent. The amount of solvent here is small, since the substituted acetylene has a much better solubility in the absorbent than acetylene. In other words, it is sufficient to prescrub the process gas with a small amount of solvent before it enters into the acetylene isolation stages described in more detail below. In the first scrubber 22, the solvent N-methyl-2-pyrrolidone is employed in order to separate off all the aromatic compounds and C4 and substituted acetylenes, apart from vinylacetylene. More precisely, the solvent N-methyl-2-pyrrolidone is employed in order to separate the process gas or the composition C1 into three streams. The first stream comprises substituted acetylenes and aromatic compounds, which are the most soluble constituents of the composition C1. The second stream comprises the valuable product acetylene, which has a poorer solubility than the substituted acetylenes but has significantly better solution properties than the remaining constituents of the composition C1. The third stream comprises crude synthesis gas, which comprises chiefly hydrogen and carbon monoxide. In the first scrubber 22, the solvent is employed in order to separate off all the aromatic compounds and C4 and the substituted acetylene virtually completely (apart from vinylacetylene).

A composition C2 is obtained by the prescrubbing in the first scrubber 22. The composition C2 comprises all the compounds which have not been separated off. In other words, the composition C2 comprises virtually no aromatic compounds, virtually no C4 compounds and virtually no substituted acetylene, with the exception of vinylacetylene. The composition C2 is fed to the second scrubber 26 via the line 24. In the second scrubber 26, the solvent is added to the composition C2 to obtain a composition C3. The amount of solvent in the second scrubber 26 here is significantly greater compared with the amount of solvent in the first scrubber 22. The larger amount of solvent dissolves the acetylene, the remaining substituted acetylene and some carbon monoxide. The second scrubber 26 is constructed such that the so-called lean gas, which comprises chiefly hydrogen and carbon monoxide, leaves the second scrubber 26 at the top end 32 of the second scrubber 26. The composition C3 thus comprises dissolved acetylene, the remaining substituted acetylene and some carbon dioxide.

The composition C3 is fed to the first stripper 36 via the line 34. The first stripper 36 is constructed for stripping the composition C3 to obtain a composition C4 and for separating off the acetylene. The composition C3 is stripped in the first stripper 36. The composition C4 which comprises the substituted acetylene, acetylene and the solvent is thereby obtained. The first stripper 36 operates slightly above ambient pressure and temperature. Carbon dioxide, which is the gas with the poorest solubility, is thereby released at the top end 40 of the stripper 36. The carbon dioxide can be recycled to the intake side of the compressor 18. The acetylene is taken off, for example, as a side stream at the side 42 of the first stripper 36.

The composition C4 is fed to the first column 46 via the line 44. Heat is supplied to the stream and the pressure is increased here in a manner such that the composition C4 in the line 44 has a pressure of from 7.5 bar to 8.5 bar and a temperature of from 125° C. to 135° C. For example, the composition C4 in the line 44 has a pressure of 8.0 bar and a temperature of 130° C. The first column 46 is constructed for partial degassing of composition C4 under a pressure of from 1.0 bar to 1.5 bar to obtain a composition C5 and a first amount A1 of the solvent. In the first column 46, the composition C4 is partially degassed under a pressure of from 1.0 bar to 1.5 bar, such as, for example, 1.35 bar. The composition C5, the first amount A1 of the solvent and a composition C10 are thereby obtained. The composition C10 formed in this way, which substantially comprises acetylene and vinylacetylene, is fed to the first stripper 36 again as stripping gas via line 52. The stripping gas in the line 52 has a pressure of from 1.30 bar to 1.40 bar and a temperature of from 110° C. to 120° C. For example, the stripping gas in the line 52 has a pressure of 1.35 bar and a temperature of 115° C. A bottom product in the first column 46 is heated via an evaporator 90. The evaporator 90 is operated such that on re-entry into the first column 46 the bottom product has a pressure of from 1.2 bar to 1.5 bar and a temperature of from 165° C. to 180° C. For example, on re-entry into the first column 46 the bottom product has a pressure of 1.4 bar and a temperature of 173° C. The gas formed in this way, which substantially contains acetylene and vinylacetylene, is fed to the first stripper 36 again as stripping gas via line 52. The stripping gas in the line 52 has a pressure of from 1.30 bar to 1.40 bar and a temperature of from 110° C. to 120° C. For example, the stripping gas in the line 52 has a pressure of 1.35 bar and a temperature of 115° C. The stripping gas is thereby cooled in the line 52 by a heat exchanger 92. Downstream of the heat exchanger 92 the stripping gas has a pressure of from 1.0 bar to 1.50 bar and a temperature of from 35° C. to 45° C. For example, downstream of the heat exchanger 92 the stripping gas has a pressure of 1.33 bar and a temperature of 40° C. The mixed condensate which can be removed from the heat exchanger 92 likewise has, in this case, a temperature of 40° C.

The composition C5 comprises vinylacetylene, methylacetylene, excess process water and the remaining solvent. The composition C5 is taken off from the first column 46 as a gaseous side stream. The water content of the solvent is monitored by the evaporator output in the first column 46. The degassing is concluded in the bottom of the first column 46 and the first amount A1 of the solvent is fed to the second scrubber 26 again via a line 94, via which the first column 46 is connected to the second scrubber 26. Alternatively or in addition, the first amount A1 of the solvent can be fed to the first scrubber 22 via a line which is not shown in more detail.

The composition C5 is fed to the second stripper 56 via the line 54. The first column 46 is operated in the manner described above. By this means, the composition C5 leaving the first column 46 at the side take-off 58 has a pressure of from 1.0 bar to 1.5 bar and a temperature of from 140° C. to 150° C. For example, the composition C5 leaving the first column 46 at the side take-off 58 has a pressure of 1.375 bar and a temperature of 147° C. In the second stripper 56, the composition C5 is fed to a composition C9, which is described in still more detail below, to obtain a second amount A2 of the solvent and a composition C6. The second amount A2 of the solvent can be fed to the second scrubber 26 again via a line 96, via which the second stripper 56 is connected to the second scrubber 26. Alternatively or in addition, the second amount A2 of the solvent can be fed to the first scrubber 22 via a line which is not shown in more detail. The third stripper 68 is constructed for stripping the solvent from the first scrubber 22 to obtain the composition C9. In the third stripper 68, the small amount of solvent from the first scrubber 22 is stripped with crude synthesis gas in order to drive out dissolved acetylene and to recycle the vapor stream to the intake side of the compressor 18 via a line 98. The composition C9 is thereby obtained. The third stripper 68 is connected to the second stripper 56 via a line 100. The composition C9 is fed to the second stripper 56 via the line 100 at its top end 62. The third stripper 68 is operated here such that the composition C9 in the line 100 has a pressure of from 1.0 bar to 1.3 bar and a temperature of from 40° C. to 55° C. For example, the composition C9 in the line 100 has a pressure of 1.22 bar and a temperature of 47.5° C. In the second stripper 56, the gaseous removed stream of the composition C5 from the first column 46 flows in counter-current to the solvent of the composition C9. At this point it is to be mentioned that the vapor stream formed in the first stripper 36 can also be recycled to the intake side of the compressor 18 via the line 98.

The apparatus 72 arranged in the vicinity of the side take-off 58 of the first column 46 for adding a diluting gas to the composition C5 adds to the composition C5 the diluting gas which is fed into line 54. The diluting gas is selected from the group consisting of $H_2$, $N_2$, $CO_2$, $NH_3$, lean gas and natural gas. For example, natural gas is fed in as the diluting gas and with a volume stream corresponding to the safety requirements. The second stripper 56 is constructed for degassing the composition C5 under a pressure of from 1.0 bar to 1.4 bar, for example 1.22 bar. Preferably, the pressure in the second stripper 56 is somewhat lower than in the first column 46, which can be controlled via the amount of diluting gas fed in. A bottom product in the second stripper 56 is heated via an evaporator 102. The evaporator 102 is operated such that on re-entry into the second stripper 56 the bottom product has a pressure of from 1.20 bar to 1.30 bar and a temperature of from 155° C. to 170° C. For example, on re-entry into the second stripper 56 the bottom product has a pressure of 1.25 bar and a temperature of 163° C. This also applies to the second amount A2 of the solvent in the line 96. The composition C6 is obtained in accordance with this procedure. The composition C6, which forms the vapor of the second stripper 56, comprises vinylacetylene, methylacetylene, excess process water and the remaining solvent.

The composition C6 is fed to the second column 76 via the line 74. By the mode of operation described above for the second stripper 56, the composition C6 in the line 74 has a pressure of from 1.0 bar to 1.4 bar and a temperature of from 120° C. to 130° C. For example, the composition C6 in the line 74 has a pressure of 1.22 bar and a temperature of 125° C. The second column 76 is constructed for adding water to the composition C6 to obtain a composition C7 comprising a third amount A3 of the solvent and water and to obtain a composition C8 comprising the substituted acetylene. In other words, the solvent still contained or remaining in the composition C6 is backwashed with a little water. The water fed to the second column 76 can be fed in with a flow rate of from 2,000 kg/h to 2,400 kg/h, for example 2,200 kg/h. The water/solvent mixture formed in this way can be fed to the main solvent stream again in the line 44. The second column 76 is operated such that the water/solvent mixture can be removed at the lower end 78 and has a temperature of from 100° C. to 110° C., for example 104° C.

The composition C8 is fed to the mixing condenser 82 via the line 80. The second column 76 is operated such that the composition C8 in the line 80 has a pressure of from 1.0 bar to 1.3 bar and a temperature of from 90° C. to 110° C. For example, the composition C8 in the line 80 has a pressure of 1.18 bar and a temperature of 100° C. The mixing condenser 82 is constructed for adding water to the composition C8 to obtain a composition C11 comprising the substituted acetylene. In the mixing condenser 82, water is added to the composition C8 to obtain the composition C11 comprising the substituted acetylene. The water fed to the mixing condenser 82 has a temperature of from 40° C. to 60° C., for example 50° C. The gaseous composition C8 is thereby cooled in the mixing condenser 82 by direct contact with water in order to condense out most of the water vapor. The water which can be removed at the lower end 86 has, in this case, a temperature of about 60° C., in particular between 40° C. and 80° C. and preferably 60° C. to 70° C., and is cooled via a heat exchanger 104 and fed to the mixing condenser 82 again with the temperature described above. Water can optionally be fed into this circulation or removed from this circulation. The substituted acetylene is removed at the top end 88 of the mixing condenser 82. In the mode of operation described, the substituted acetylene removed at the top end 88 of the mixing condenser 82 has a pressure of from 1.0 bar to 1.3 bar and a temperature of from 45° C. to 65° C. For example. the substituted acetylene removed at the top end 88 of the mixing condenser 82 has a pressure of 1.15 bar and a temperature of from 50° C. to 60° C.

By the mode of operation described for the apparatus 10 under normal pressure, the conventional vacuum machine for compressing the composition C10 and the gas machine and cooling apparatus for compressing the composition C11 become superfluous. Instead, a safer and less expensive mode of operation under normal pressure or slight excess pressure results. As a result, the critical point for naphthalene shifts into the mixing condenser 82. The temperature in the mixing condenser 82 is therefore established such that a precipitation of naphthalene is prevented. The bottom temperature is established at, for example, 60° C. to 70° C., as a result of which the precipitation of naphthalene is avoided. Downstream of the mixing condenser 82, the distance from the dew point can be increased by dilution with, for example, natural gas or lean gas, so that condensation on the way to the torch can be avoided.

LIST OF REFERENCE SYMBOLS

10 Apparatus
12 Reactor
14 Burner block
16 Line
18 Compressor
20 Line
22 First scrubber
24 Line
26 Second scrubber
28 Top end
30 Lower side end
32 Top end
34 Line 36 First stripper
38 Lower end
40 Top end
42 Side
44 Line
46 First column
48 Lower end
50 Top end
52 Line
54 Line
56 Second stripper
58 Side take-off
60 Lower end
62 Top end
64 Lower end
66 Line
68 Third stripper
70 Top end
72 Apparatus for feeding in a diluting gas
74 Line
76 Second column
78 Lower end
80 Line
82 Mixing condenser
84 Top end
86 Lower end
88 Top end
90 Evaporator
92 Heat exchanger
94 Line
96 Line
98 Line
100 Line
102 Evaporator
104 Heat exchanger

The invention claimed is:

1. An apparatus for preparation of acetylene and synthesis gas by partial oxidation of hydrocarbons with oxygen, comprising:
a reactor, wherein the reactor comprises a burner block with a furnace chamber for the preparation of a composition C1 comprising at least acetylene and substituted acetylene;
a first scrubber which is constructed for adding a solvent to the composition C1 to obtain a composition C2;
a second scrubber which is constructed for adding a solvent to the composition C2 to obtain a composition C3;
a first stripper which is constructed for stripping the composition C3 to obtain a composition C4 comprising the substituted acetylene, acetylene and the solvent and for separating off the acetylene;
a first column which is constructed for partial degassing of the composition C4 under a pressure of from 1.0 bar to 1.5 bar to obtain a composition C5, a composition C10 and a first amount A1 of the solvent;
a second stripper to which the composition C5 can be fed for stripping a composition C9 to obtain a second amount A2 of the solvent and a composition C6;
a third stripper which is constructed for stripping the solvent from the first scrubber to obtain a composition C9, the third stripper being connected to the second stripper for feeding the composition C9 to the second stripper,
wherein an apparatus for adding a diluting gas to the composition C5 is arranged between the first column and the second stripper;
a second column which is constructed for adding water to the composition C6 to obtain a composition C7 comprising a third amount A3 of the solvent and water and to obtain a composition C8 comprising the substituted acetylene; and
a mixing condenser which is constructed for adding water to the composition C8 to obtain a composition C11 comprising the substituted acetylene.

2. The apparatus as claimed in claim 1, wherein the diluting gas is selected from the group consisting of: $H_2$, $N_2$, $CO_2$, $NH_3$, lean gas, and natural gas.

3. The apparatus as claimed in claim 1, wherein the second amount A2 of the solvent obtained from the second stripper can be fed to the first and/or second scrubber.

4. The apparatus as claimed in claim 1, wherein the first content A1 of the solvent obtained from the first column can be fed to the first and/or second scrubber.

5. The apparatus as claimed in claim 1, wherein the first column has a side take-off for leading off the composition C5, wherein the apparatus for adding a diluting gas to the composition C5 is adjacent to the side take-off.

6. The apparatus as claimed in claim 1, wherein a temperature is established in the mixing condenser for preventing a precipitation of naphthalene.

7. The apparatus as claimed in claim 6, wherein the tee temperature in the mixing condenser is from 40° C. to 80° C.

8. The apparatus as claimed claim 1, wherein the second stripper for degassing the composition C9 can be operated under a pressure of from 1.0 bar to 1.4 bar.

9. The apparatus as claimed in claim 1, wherein the solvent is N-methyl-2-pyrrolidone.

10. A process for preparing acetylene and synthesis gas by partial oxidation of hydrocarbons with oxygen, the process comprising:
partially oxidizing hydrocarbons with oxygen for the preparation of a composition C1 comprising at least acetylene and substituted acetylene;
adding a solvent to the composition C1 to obtain a composition C2;
adding the solvent to the composition C2 to obtain a composition C3;
stripping of the composition C3 to obtain a composition C4 comprising the substituted acetylene, acetylene and the solvent and to separate off the acetylene from the composition C3;
partial degassing of the composition C4 under a pressure of from 1.0 bar to 1.5 bar to obtain a composition C5, a composition C10 and a first amount A1 of the solvent;
stripping of a composition C9 with the composition C5 to obtain a second amount A2 of the solvent and a composition C6;
stripping of the solvent obtained after preparation of the composition C2 to obtain the composition C9;
adding a diluting gas to the composition C5;
adding water to the composition C6 to obtain a composition C7 comprising a third amount A3 of the solvent and water and to obtain a composition C8 comprising the substituted acetylene; and
adding water to the composition C8 to obtain a composition C11 comprising the substituted acetylene.

11. The process as claimed in claim 10, wherein the diluting gas is selected from the group consisting of: $H_2$, $N_2$, $CO_2$, $NH_3$, lean gas, and natural gas.

12. The process as claimed in claim 10, wherein the second amount A2 of the solvent obtained is fed to the composition C1 and/or C2.

13. The process as claimed in claim 10, wherein the first amount A1 of the solvent obtained is fed to the composition C1 and/or C2.

14. The process as claimed in claim 10, wherein the water is added to the composition C8 in a mixing condenser, wherein a temperature is established in the mixing condenser for preventing a precipitation of naphthalene.

15. The process as claimed in claim 14, wherein the temperature is from 40° C. to 80° C.

16. The process as claimed in claim 10, wherein the composition C9 is degassed under a pressure of from 1.0 bar to 1.4 bar.

17. The process as claimed in claim 10, wherein the solvent is N-methyl-2-pyrrolidone.

* * * * *

UNITED STATES PATENT AND TRADEMARK OFFICE
CERTIFICATE OF CORRECTION

Page 1 of 1

PATENT NO. : 10,059,640 B2
APPLICATION NO. : 15/129094
DATED : August 28, 2018
INVENTOR(S) : Maximilian Vicari et al.

It is certified that error appears in the above-identified patent and that said Letters Patent is hereby corrected as shown below:

In the Specification

In Column 11, Line 6, delete "a the" and insert -- the --, therefor.

In the Claims

In Column 16, Line 25, Claim 7, after "wherein the" delete "tee".

In Column 16, Line 28, Claim 8, after "claimed" insert -- in --.

Signed and Sealed this
Twenty-second Day of October, 2019

Andrei Iancu
*Director of the United States Patent and Trademark Office*